United States Patent [19]

Islam et al.

[11] Patent Number: 5,674,006
[45] Date of Patent: Oct. 7, 1997

[54] FLUID CIRCULATION APPARATUS

[75] Inventors: Mohammed Rezaul Islam, Sunnyvale; Richard Alan Flanagan, Berkeley; Urs Steiner, Sunnyvale, all of Calif.; Hélène Bredberg-Davies; Hilary Davies, both of Lidingö, Sweden

[73] Assignee: Hoefer Pharmacia Biotech, Inc., San Francisco, Calif.

[21] Appl. No.: 622,382

[22] Filed: Mar. 27, 1996

[51] Int. Cl.$^6$ ..................................................... B01F 11/00
[52] U.S. Cl. .......................... 366/239; 366/131; 366/211; 206/219; 422/99; 422/102
[58] Field of Search ..................................... 366/108, 110, 366/111, 112, 128, 210, 211, 215, 218, 131, 137, 237, 239, 182.1, 182.2, 182.3, 240, 349; 206/219, 557, 563; 220/201, 570, 669; D7/354, 550, 586, 587; 422/99, 100, 102

[56] References Cited

U.S. PATENT DOCUMENTS

| | | | |
|---|---|---|---|
| 2,494,866 | 1/1950 | Fressola | 366/210 |
| 2,877,700 | 3/1959 | Keller | 366/239 |
| 3,784,056 | 1/1974 | Spruyt et al. | 221/63 |
| 4,026,531 | 5/1977 | Luchsinger et al. | 366/211 |
| 4,155,477 | 5/1979 | Fosher | 220/4.27 |
| 4,784,297 | 11/1988 | Katz | 366/211 |
| 4,839,684 | 6/1989 | Michelson et al. | 366/211 |
| 5,353,930 | 10/1994 | Berry, Jr. | 206/557 |

FOREIGN PATENT DOCUMENTS

| | | | |
|---|---|---|---|
| 567182 | 12/1958 | Canada | 366/240 |
| 328563 | 10/1920 | Germany | 366/237 |
| 4039354 | 6/1992 | Germany | 206/557 |

OTHER PUBLICATIONS

Brochure AutoMate Scientific, Jun. 1993, "Gel/Blot Washing System".
Brochure SLT (undated) "profiBLOT Western Blot strip processor".
Brochure, Biomedical Products, Dec. 1996, "AutoBlot 2000".
1995–1996 Atto Corporation Catalog, pp. 74, 75.

Primary Examiner—Tony G. Soohoo
Attorney, Agent, or Firm—Limbach & Limbach

[57] ABSTRACT

An apparatus for efficiently circulating and moving a fluid across a workpiece. The apparatus can provide for the automated handling of the fluids used, and is well suited for use in the staining and fixing of biological assays such as electrophoresis gels. The tray of the invention includes first and second side walls, first and second end walls, a first curved wall portion connecting the first side wall and the first end wall, and a second curved wall portion connecting the second side wall and the second end wall. The inclusion of the curved surface in the combination causes mixing to occur efficiently when the tray is "rocked" from side to side as in the conventional apparatus. Thus, the apparatus of the invention may also include a motor for alternately raising and lowering each end wall of the tray in a rocking motion, thereby causing the fluid to alternately flow towards and away from each end wall. The apparatus can include an automated means for supplying fluid to and from the tray to one or more containers.

31 Claims, 4 Drawing Sheets

PROCESSING STEP

FIG. 2B

FILLING AND EMPTYING STEP

FLUID CIRCULATION APPARATUS

BACKGROUND

The present invention relates to an apparatus for circulating a fluid about a workpiece. More specifically, the invention relates to an apparatus for the staining and fixing of biological assays such as electrophoresis gels.

Gel electrophoresis is an important biological assay, which takes advantage of the fact that different molecules applied to a gel migrate at different rates when they are subjected to an electric field. After the biological molecules have been separated in this manner they must be detected, i.e. the gel must be read. The detection may be accomplished in a variety of ways including visible staining, fluorescence staining, and radioactive labeling. It may also be necessary to fix the gel, which will render the gel stable for extended periods of time.

In both staining and fixing techniques the gel is placed in contact with a reagent solution and the biological molecules either chemically or physically react with the active ingredients of the solution. To avoid the gradual slowing of the reaction due to depletion of the active ingredient in the vicinity of the biological molecules, it is desirable to keep the fluid well mixed during the process. Furthermore, the more efficiently the mixing brings fresh reagent in contact with the biological molecules, the shorter the time required for the processing step. Since staining and fixing are time consuming and labor intensive processes, any improvement in the efficiency of reagent mixing during processing will lead to time, and therefore, cost savings.

There are commonly two apparatus used in the staining and fixing of gels: the conventional rocker and the conventional shaker.

In the conventional rocker, the gel is placed in a rectangular tray together with the staining or fixing reagent and the tray is then tipped (or "rocked") from side to side to circulate the reagent across the gel. To achieve efficient mixing the amplitude—or maximum angle—of the tipping must be substantial and, since the gel must remain submerged at all times, this method therefore requires a large volume of reagent. Conversely, if the volume of reagent is reduced the tipping amplitude must also be reduced, which reduces the mixing efficiency and hence increases the time for the processing step.

In the conventional shaker, the gel is placed in a rectangular tray together with the reagent solution and the tray is shaken with a circular motion. In this apparatus the tray is held horizontal at all times and so does not require the excessive volumes of reagent required by the conventional rocker. However, mixing is less efficient near the center of the tray and in some staining or fixing steps the mixing efficiency of the conventional shaker is the limiting factor in the time required for the processing step. This is also true of the conventional rocker and the limited mixing efficiency is a drawback of both conventional apparatus.

Another drawback of both conventional apparatus is that they must be emptied and filled with reagents manually. This is time consuming, labor intensive, and can be hazardous, since toxic or radioactive reagents are sometimes used.

For these reasons, it is an object of the invention to provide an apparatus for the processing of a sheet-shaped workpiece, such as an electrophoresis gel, which minimizes the volume of reagent solution used and can efficiently circulate and mix the reagents across the workpiece thus continually exposing the workpiece to fresh reagent. It is a further object of the invention to provide an apparatus which can automatically be loaded, drained and recharged with a reagent-containing fluid.

SUMMARY

In order to meet these objects, the present invention provides an apparatus for efficiently circulating and moving a fluid across a workpiece. Additionally, the apparatus of the invention provides for the automated handling of the fluids used. The apparatus of the present invention is well suited for use in the staining and fixing of biological assays such as electrophoresis gels.

In one embodiment the apparatus comprises a tray having first and second side walls, first and second end walls, a first curved wall portion connecting the first side wall and the first end wall, and a second curved wall portion connecting the second side wall and the second end wall. The tray can then be rocked by alternately raising and lowering each end wall which causes fluid to alternately flow towards and away from each end wall.

In another embodiment, the first and second end walls of the tray are parallel and the first and second side walls are parallel and an imaginary plane extending from the first side wall and an imaginary plane extending from the first end wall intersect with an inner angle of greater than 90°.

Preferably, in the tray of the invention, the end walls have approximately equal lengths and the curved wall portions have approximately equal lengths, and the length of the end walls are approximately equal to the length of the curved wall portions. Overall, however, in this embodiment, the ratio of the length of the end walls to the length of the curved wall portions can range from about 2:3 to about 3:2.

Advantageously, the tray further includes a base having one or more ports, which can be used to move fluid into and/or out of the tray. It is also advantageous if the tray base and a lower portion of each tray wall are joined by a curved connection.

The tray of the invention can form part of a fluid mixing apparatus which further includes a platform for supporting the tray, and a means for alternately raising and lowering each end wall of the tray mounted on the platform (such as a motor).

The fluid mixing apparatus may also include means for filling the tray with fluid from a selected container and emptying the tray of fluid into a selected container. Such filling and emptying means can include a control valve for selectively connecting one of the containers to the tray port and a pump connected in-line between the tray port and the selected container.

In another embodiment, the control valve can include an output connected to the tray port and one or more inputs connected to the one or more containers.

In a further embodiment, the apparatus according to the invention can include a control system coupled to the means for alternately raising and lowering the end walls, the pump, and the control valve. The control system controls the timing of one or more processing or filling/emptying steps, such that during a processing step the raising/lowering means (such as a motor) is controlled to alternately raise and lower the end walls and during a filling/emptying step the pump and control valve are controlled to fill the tray with fluid from a selected container, or empty the tray of fluid into a selected container.

BRIEF DESCRIPTION OF THE DRAWINGS

The invention will be better understood by reference to the appended figures, in which.

In these figures, the same reference number denotes identical or corresponding parts.

DETAILED DESCRIPTION

Preferred embodiments of the invention will now be described in detail, with reference to the figures.

Figure 1:
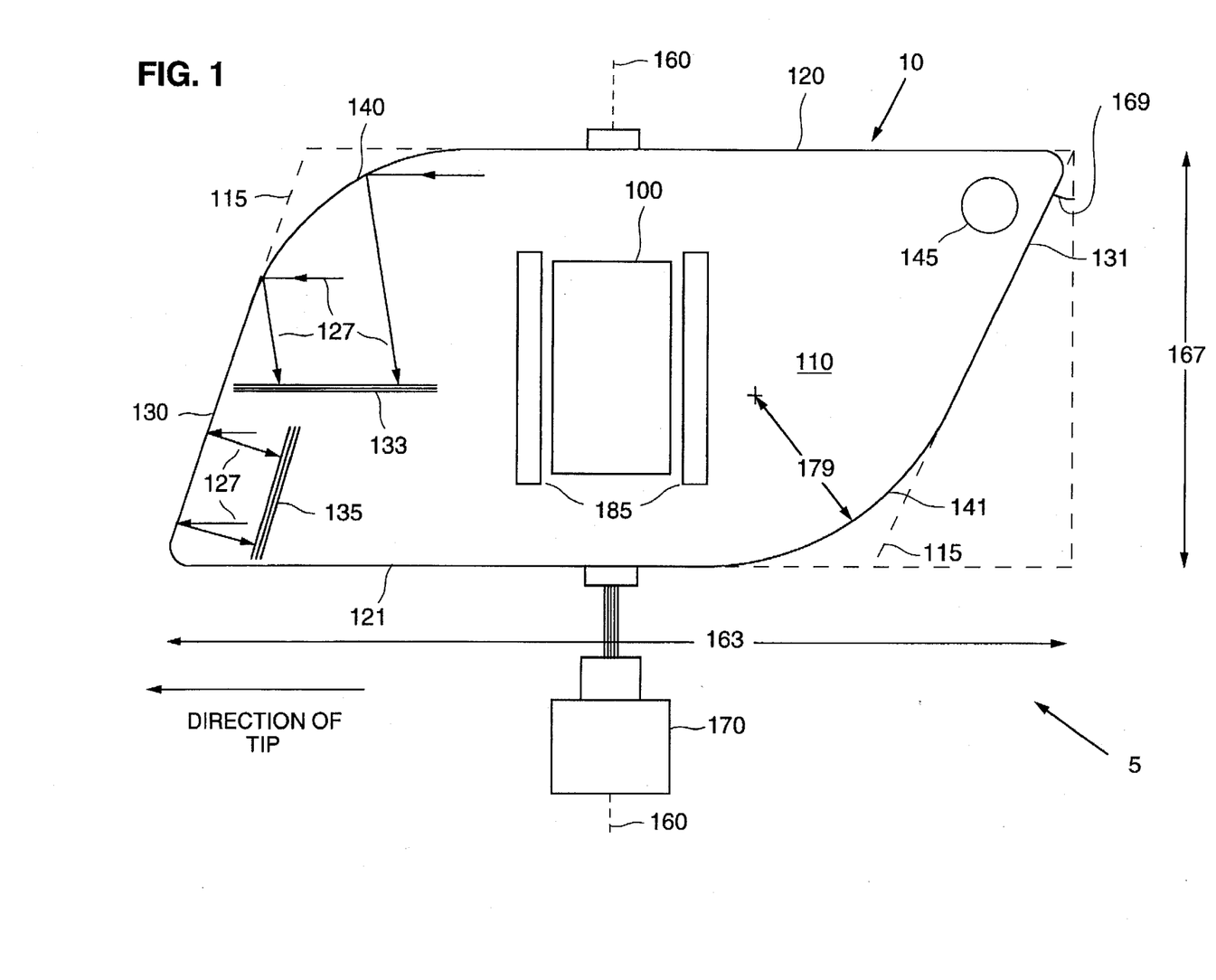
FIG. 1 shows a top view of a first embodiment of the invention.
Figure 2A:
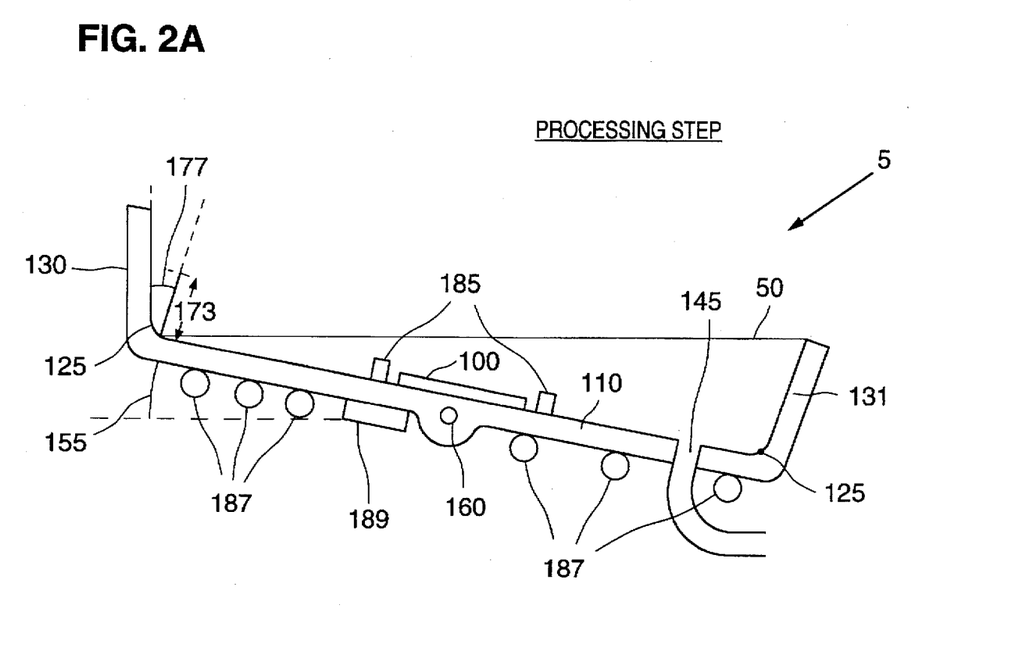
FIGS. 2A and 2B show cross-sectional views of the embodiment shown in FIG. 1.
Figure 2B:
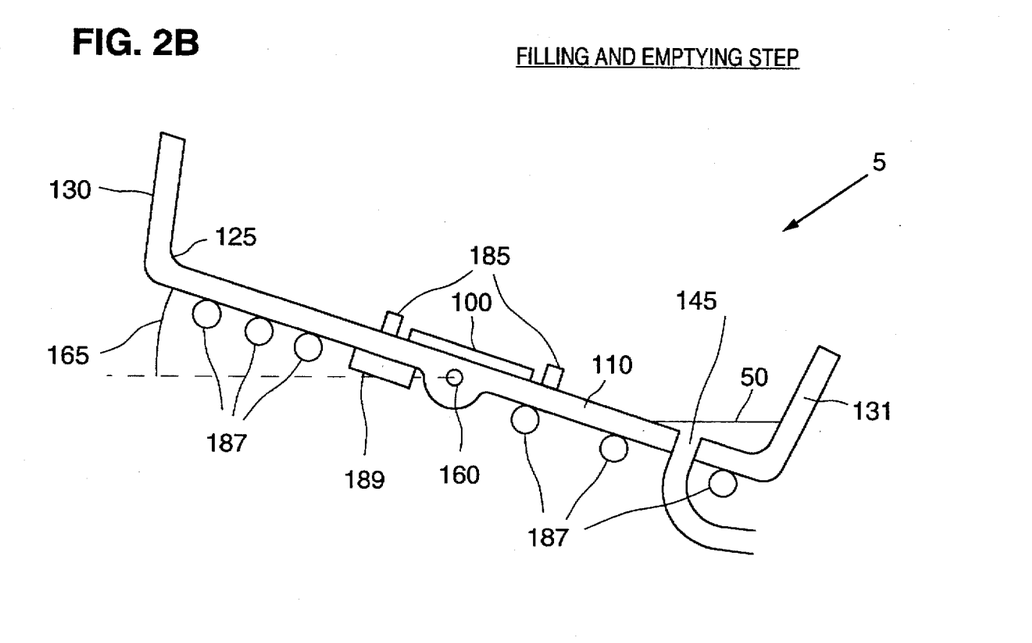

FIGS. 1, 2A, and 2B show an apparatus 5 for circulating a fluid across a workpiece. The apparatus includes a means for containing the fluid and the workpiece (typically sheet-shaped) which includes a tray 10 for holding a fluid 50 and a workpiece 100. The tray includes a base 110, first and second side walls 120 and 121, first and second end walls 130 and 131, a first curved wall portion 140 connecting the first side wall and the first end wall, and a second curved wall portion 141 connecting the second side wall and the second end wall. The walls of the tray meet the base in a connection 125. The tray is pivoted about an axis 160 and is connected to a motor 170 for alternately raising and lowering each end wall. The tray base may also include a port 145 which may be situated adjacent to an acute angled corner of the tray. The workpiece 100 may be constrained from moving by use of a "fence" 185. The apparatus may further include a heater/cooler coil 187 for heating or cooling the fluid, and a temperature monitor 189 for monitoring the temperature of the fluid. The heater or cooler, and temperature monitor are for controlling the temperature of the fluid.

Figure 4:
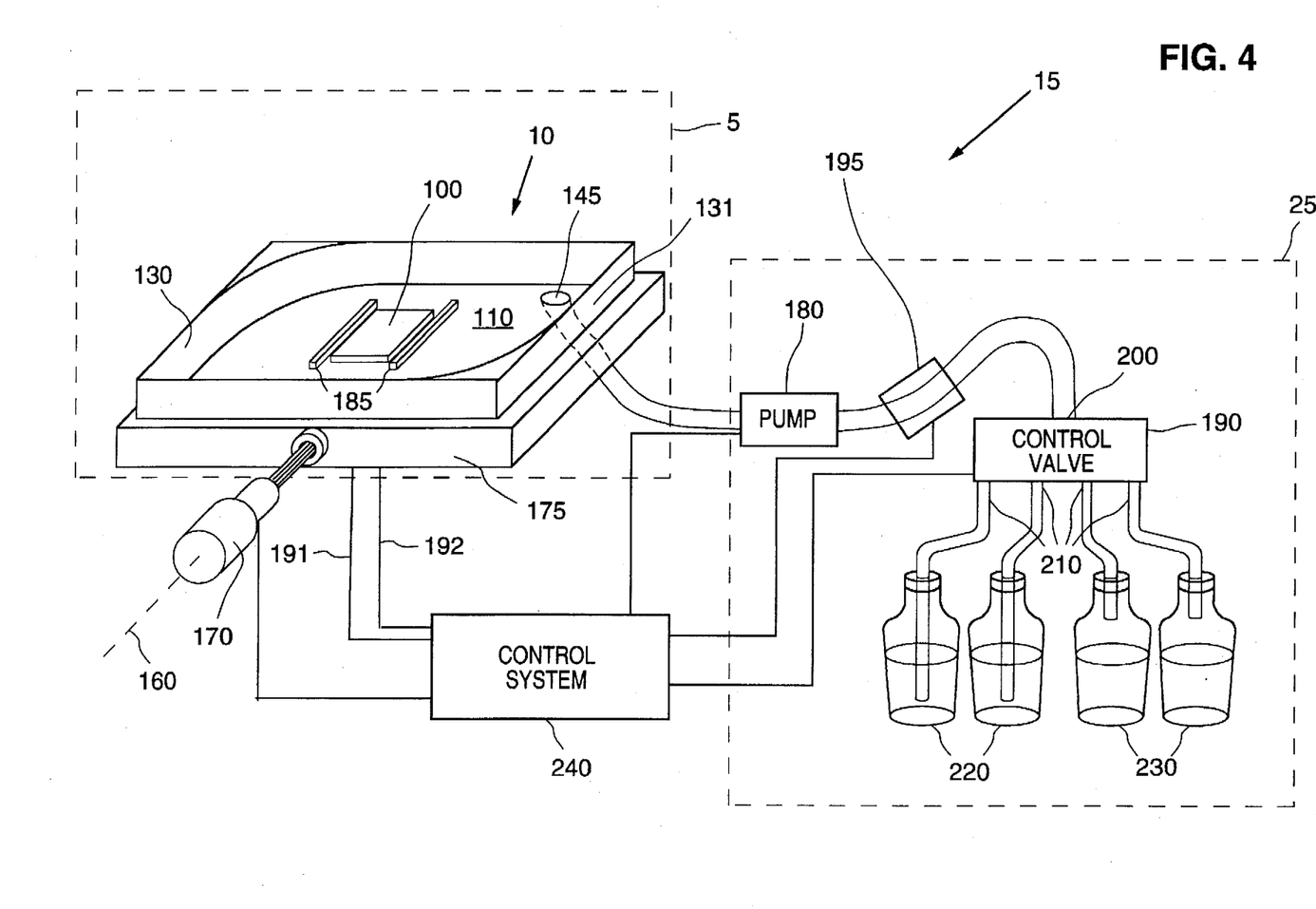
FIG. 4 shows a simplified perspective top view of a second embodiment of the present invention.

Tray 10 may have a cover (not shown) and may be supported on a platform (see FIG. 4, 175). The tray 10 may be fabricated from any structurally rigid material which is inert with respect to the fluid, as is conventional. Examples of suitable materials are various plastic materials, glass, and stainless steel. For use in gel staining, the tray is preferably fabricated from stainless steel. The tray, as viewed from above, is generally parallelogram shaped 115 with substantially rounded obtuse angled corners 140 and 141.

The tray walls 120, 121, 130, 131, 140, and 141 may be perpendicular to the base 110 or may be inclined at an angle 177 (FIG. 2A). The connection 125 between the walls and the base may be sharp or rounded. It is preferred that the connection 125 is rounded so that the fluid is not trapped in the connection when thee tray is rocked. A rounded connection 125 is also more easily fabricated if the tray is manufactured in one piece.

There are two preferred sizes of tray (for work with electrophoresis gels): in a first embodiment the tray dimensions (i.e. lengths 163 and 167 in FIG. 1) are about 310 mm by about 195 mm; and in a second embodiment the tray dimensions are about 380 mm by about 295 mm. In both preferred embodiments, the angle 169 is about 5° and the depth 173 of the tray is about 25 mm. For clarity, the angle 169 is exaggerated in FIG. 1. In both embodiments all of the wall portions make an angle 177 of about 5° with the base. In the first embodiment the radius of curvature 179 of the curved wall portions is about 60 mm and in the second embodiment the radius is about 115 mm. In the first embodiment the approximate lengths of the curved wall portions 140 & 141, the side walls 120 & 121, and the end walls 130 & 131 are about 90 mm, 250 mm, and 135 mm respectively. In the second embodiment these lengths are about 180 mm, 265 mm, and 185 mm respectively.

The pivot axis 160 is preferably perpendicular to a pair of sides of the tray. This ensures that substantially equal mixing occurs when the tray is rocked to the left and the right.

Motor 170 is capable of alternately raising and lowering each end wall when the tray contains the workpiece and the fluid. The means for alternately raising and lowering each end wall may be connected directly to the tray (FIGS. 1 and 2) or, if the tray is supported on a platform, it may be connected to the platform (see FIG. 4).

Figure 3A:
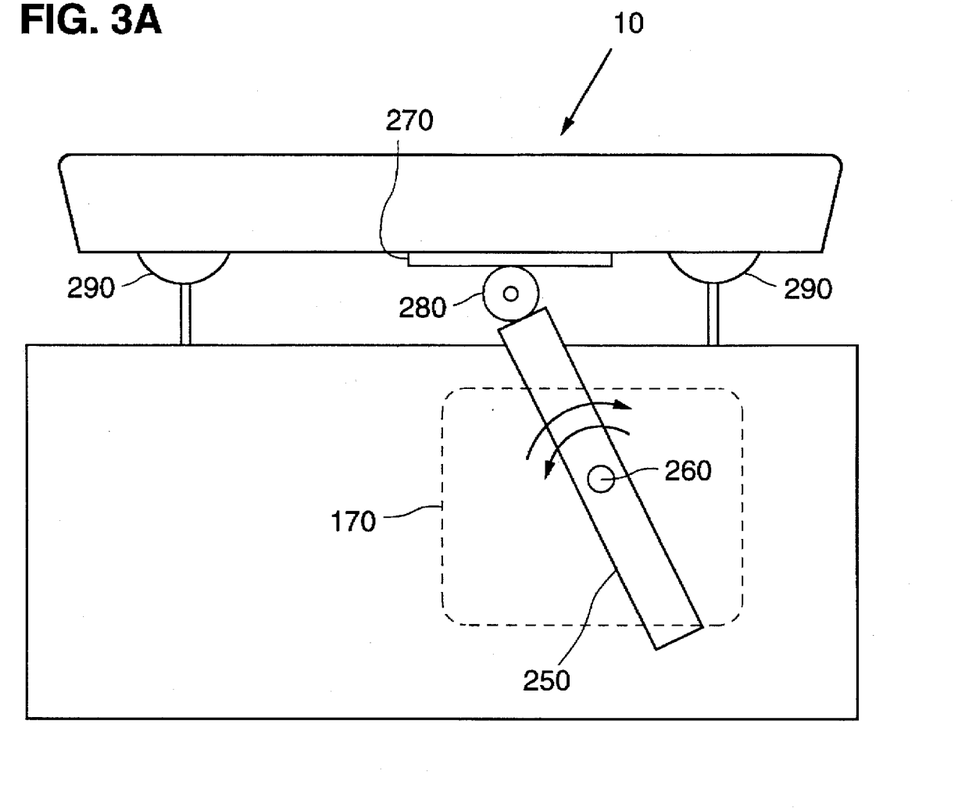
FIGS. 3A and 3B show back and side views of an embodiment of the means for alternately raising and lowering each end wall.
Figure 3B:
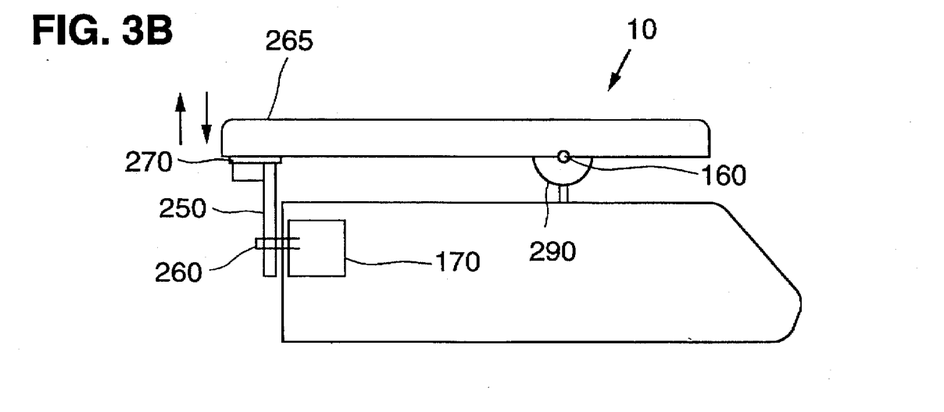

FIGS. 3A and 3B show one embodiment of a means suitable for alternately raising and lowering each end wall of the tray. This embodiment includes a stepper motor 170 connected to a rocking finger 250 via a shaft 260. One end 265 of the tray rests on a support 270 which is connected to the rocking finger 250 via a ball bearing joint 280. The tray also rests on pivots 290. In operation, the motor causes the rocking finger to alternately rotate in a clockwise and anticlockwise direction which causes the support 270 to slide back and forth under the tray. In this way, end 265 of the tray is alternately raised and lowered and the tray is pivoted about axis 160.

Port 145 can be used for adding and removing the fluid. The port is positioned so that when the tray is tipped to one side the port is close to the lowest point of the tray. In this way, the tray is most easily emptied and filled through the port. The parallelogram shape of the tray allows efficient draining by tilting the tray about the rocking axis 160. In contrast, to efficiently drain a rectangular tray it is necessary to tilt the tray about an axis that is not perpendicular to either pair of sides. The tray base may include more than one port. For example, the tray base may include one port through which the tray is filled with fluid and one port through which the tray is emptied of fluid.

Workpiece 100 may be held in place using a fence 185, which is capable of constraining the movement of the workpiece during processing without substantially interfering with circulation of the fluid, as is conventionally known. The fence may be detachable from the base or may be integral with the base. Furthermore, if it is detachable, it is advantageous that it be capable of accommodating workpieces of different sizes and at different positions in the tray. The fence may be fabricated from any material that is inert with respect to the fluid. If the tray is fabricated from any magnetizable material, the fence 185 may be constructed to include magnets. Alternatively, a sheet of soft steel (magnetic) may be attached to the underside of the base of a tray made of non-magnetizable material and the fence 185 may then also be constructed to include magnets.

The apparatus may further include a heater for heating the fluid, a cooler for cooling the fluid, and a temperature monitor for monitoring the temperature of the fluid. FIG. 2A and 2B shows one embodiment in which heating and cooling of the fluid is accomplished using a heater/cooler coil 187 attached to the underside the tray. In this embodiment the temperature of the fluid is monitored using a temperature monitor 189 attached to the underside of the tray. The heater, cooler, and temperature monitor may also be located inside the tray in contact with the fluid, or they may be integral with the tray. In addition to the heating coil shown in FIG. 2A and 2B, a resistance heater may be used in the present invention.

In operation, the apparatus of the invention is used as follows. First, the fluid and the workpiece are placed in the tray. The fluid may be placed in the tray either manually or automatically (as is described below with reference to FIG. 4). Next, motor 170 is activated, thereby alternately raising and lowering each end wall. This rocking motion causes the fluid to alternately flow towards and away from each end wall. The rocking motion ensures that the fluid is continuously mixed and circulated across the workpiece. In this way, the workpiece is continuously in contact with fresh fluid. As in prior mixing devices, the efficiency of the mixing of the fluid depends on the frequency and amplitude of the rocking (or shaking) and on the geometry of the tray.

The rocking frequency must be high enough to ensure that the fluid is kept in continual motion: flowing from one side of the tray to the other. However, if the rocking frequency is too high the rocking will not cause any motion of the fluid. The rocking frequency will depend on the size of the tray. For a tray of a size which would be typical for lab bench use (i.e., a tray having lengths 163 and 167 of approximately 310 mm by 195 mm or 380 mm by 295 mm) the frequency can be between about 15 and about 60 rocks per minute; preferably, about 30 rocks per minute.

The rocking amplitude, i.e. the maximum rocking angle 155, must be large enough to cause sufficient fluid flow to ensure efficient mixing but must not be so large that fluid splashes over the side of tray or so large that the workpiece does not remain submerged during processing. The maximum angle will depend on the height of the walls, the capacity of the tray, and the volume of fluid. In the preferred embodiments of the present invention, the rocking amplitude will be less than about 5° and most preferably about 2°.

The present inventors have found that a generally parallelogram shaped tray with substantially rounded obtuse angled corners is more efficient at mixing the fluid than a rectangular tray. To maximize the working area of the tray the angle between the side wall and the end wall is as close to 90° as possible while still maintaining efficient mixing (i.e. angle 169 is as close to 0° as possible). The inventors have found that the preferred embodiments with an angle 169 of about 5° satisfy the competing criteria of maximizing the tray area and maintaining efficient mixing. For the parallelogram shaped tray of the present invention, the efficient mixing is due to the following: when the tray is tipped, the rounded corners (140 and 141) reflect the fluid in one direction and the end walls (130 and 131) reflect the fluid in a different direction. FIG. 1 shows the direction of fluid flow 127 when the tray is tipped in the direction indicated. Fluid impinging on the rounded corner 140 is reflected with an approximate wave front 133, whereas fluid impinging on the end wall 130 is reflected with an approximate wave front 135. The interference of these reflected waves results in efficient mixing of the fluid. The substantial rounding of the first and second curved wall portions 140 and 141 must therefore be capable of producing reflected waves traveling in a different direction than the waves reflected from the end walls 130 and 131. Furthermore, efficient mixing may be accomplished if the volume of fluid reflected from the curved wall portions is comparable to the volume of fluid reflected from the end walls. To achieve these requirements in the embodiment shown, it is preferred that the length of the end walls should be approximately equal to the length of the curved wall portions. By "approximately equal" it is meant that, for example, a workable range of the ratio of the lengths of the end wall portions to the length of the curved wall portions from about 2:3 to 3:2, with about 1:1 being preferred.

The ratios of lengths in these embodiments are indicative of the range and magnitude contemplated in the present invention; however, other ratios which can achieve good mixing could readily be determined for different sized trays. It is desirable to maximize the working area of the tray, which is accomplished by reducing the length of the curved wall portion while still maintaining efficient mixing. The geometry and lengths of the end wall and curved wall portion are chosen to producing efficient mixing and may be determined using the following criteria. First, the end wall and curved wall portion must be capable of reflecting two volumes of fluid in two different intersecting directions. This ensures that the reflected volumes of fluid will mix. Second, the relative volumes of the reflected fluid must be such that efficient mixing occurs when the volumes intersect and mix. Since the volume of fluid reflected by a wall portion is proportional to the length of the wall portion, the second criteria translates into a restriction on the relative lengths of the end and curved wall portions.

In the embodiment shown in FIG. 1 the curved wall portions have a radius of curvature that is approximately equal to the dimensions of the end walls of the tray. However, from the foregoing discussion, it can be appreciated that other geometries are capable of the efficient mixing of the present invention. For example, a tray geometry capable of reflecting comparable volumes of fluid in two or more different intersecting directions will produce the efficient mixing of the present invention. One specific example may be obtained from the embodiment shown in FIG. 1 by increasing the radius of curvature of the curved wall portions until they are approximately flat while keeping the lengths of the curved wall portions approximately equal to the lengths of the end walls. This new tray shape will still reflect comparable volumes of fluid in different intersecting directions and will therefore result in the efficient mixing envisioned in the present invention.

In another embodiment of the invention, the steps of filling the tray with fluid, processing the workpiece, and draining the tray of fluid are controlled automatically. This embodiment will now be described with reference to FIG. 4, which shows an apparatus 15 for circulating a fluid across a workpiece, the fluid being supplied from, and discharged into, one or more containers. The apparatus 15 includes the following: a means 5 for containing a fluid and a workpiece, which includes a tray 10 having first and second end walls 130 and 131; a means 170 for alternately raising and lowering each end wall of the tray; and a means 25 for filling the tray with fluid from a selected container and emptying the tray of fluid into a selected container. The tray further includes a base 110 that includes a port 145 for adding and removing the fluid. The tray may optionally be supported on a platform 175. The apparatus further includes the following: a control valve 190 for selectively connecting one of the containers 220 and 230 to the tray port 145, the control valve having an output 200 and one or more inputs 210; a pump 180 connected in-line between the tray port and the selected container and a control system 240 coupled to the means for alternately raising and lowering the end walls, the pump, and the control valve. The apparatus may also include a flow sensor 195 for monitoring the flow of fluid, which may be coupled to the control system. The apparatus may further include a heater or cooler and a temperature monitor (not shown) which are for controlling the temperature of the fluid. The heater or cooler, and temperature monitor may be coupled to the control system via control lines 191 and 192.

In the embodiment shown in FIG. 4, the means 5 for containing the fluid and the workpiece includes a tray 10 that is supported on a platform 175. The motor 170 for alternately raising and lowering the end walls 130 and 131 is connected to the platform 175 and rocks the platform about an axis 160 thereby alternately raising and lowering each end wall of the tray. If the apparatus does not include a platform, the motor 170 will be connected directly to the tray, as is shown in FIGS. 1 and 2. The motor is preferably connected to the finger rocking mechanism described earlier and shown in FIGS. 3A and 3B.

The tray 10, platform 175, and motor 170 may be as previously described and exemplified in FIGS. 1 and 2. As in the previous embodiment, the apparatus may optionally include a fence for securing the workpiece and a heater or cooler, and a temperature monitor for controlling the temperature of the fluid.

The control valve 190 is capable of selectively connecting one of the containers 220 & 230 to the tray port 145. The control valve has one or more inputs 210 connected to the containers 220 & 230 and an output 200 connected to the tray port 145. The control valve is fabricated from materials that are inert with respect to the fluids used. Examples of suitable materials are glass, plastic, and stainless steel. Preferably the control valve is fabricated from stainless steel. A suitable control valve is the PhastSystem® control valve manufactured by Pharmacia Biotech.

The containers 220 & 230 are capable of containing the reagents to be supplied to the tray and the waste fluid drained from the tray. The containers may be any containers suitable for containing the reagents and waste fluids that are inert with respect to these fluids. Examples of suitable containers are glass or plastic bottles. The different reagents and washing fluids to be supplied to the tray are held in separate containers. Also, since different reagents have different disposal requirements, it may be advantageous to discharge aqueous, organic, toxic, and radioactive wastes into different containers. The containers are connected to the control valve inputs 210 and the control valve selects a container by connecting a selected control valve input 210 to the control valve output 200.

The pump is capable of pumping fluid from the selected container into the tray during tray filling and pumping fluid from the tray into the selected container during tray emptying. In one embodiment of the invention, a peristaltic pump is used.

The control system 240 is for controlling one or more filling, processing, and draining steps. During a processing step the motor 170 is controlled to alternately raise and lower the end walls and the pump 180 is controlled not to pump. During a filling or emptying step the motor may be controlled to hold the tray stationary at the filling/emptying angle (See FIG. 2, 165), and the pump and control valve are controlled to fill the tray with fluid from a selected container, or empty the tray of fluid into a selected container.

The control system may include a programmable microprocessor capable of using writable stored programs for controlling the motor, pump and control valve, and, if present a heater or a cooler, and, further, monitoring and responding appropriately to abnormal indications from a flow sensor. The apparatus may have a bidirectional communication port for connection of the microprocessor to an external channel through which programs and instructions may be transmitted to the control system. Likewise, the control system may report the status of the pump, motor, control vale, and if present, temperature and flow sensor information as well as other diagnostic information through the same communication channel to an external device. Such a bidirectional communication port also simplifies and reduces the cost of manufacture, testing, and servicing of the invention.

In one embodiment of the invention, the apparatus shown in FIG. 4 operates as follows: first, the workpiece is placed in the tray, which is empty of fluid; second, the control system controls a filling step in which a preselected quantity of a reagent is pumped from a preselected container into the tray; third, the control system controls a processing step in which the motor rocks the tray for a predetermined time; and fourth, the control system controls an emptying step in which the used reagent is pumped from the tray into a preselected container. The control system may subsequently control a preselected sequence of filling/processing/emptying cycles in which the tray is filled with a preselected reagent, rocked for a preselected time, and emptied into a preselected container. The order and number of the filling/processing/emptying cycles and the details of each cycle are programmed into the control system before operation is commenced. In this way, the processing of the workpiece is completely automatic and this will increase both the efficiency and the safety of the apparatus.

We now describe the filling, processing, and emptying steps in more detail.

In the filling step, if it is desirable to initiate the processing only after the filling is complete, the empty tray may be held fixed with the port 145 below the horizontal and the tray making a filling/emptying angle (FIG. 2B, 165) with the horizontal. Alternatively, the tray may be rocked during filling to minimize the elapsed time of processing. In one embodiment of the invention the filling/emptying angle is 5°; however, the filling and emptying angles need not be equal. The control system controls the control valve which connects a selected input 210 to the output 200 and thus connects the selected reagent container 220 to the tray port 145. The control system then controls the pump to pump fluid from the selected container into the tray through the tray port. The pump is controlled to fill the tray with a preselected quantity of fluid. This may be achieved by controlling the pump to pump for either a preselected length of time, or until a preselected volume of fluid has been pumped. If the pump is controlled to pump a preselected volume of fluid, the apparatus must further include a flow sensor to measure the volume of fluid pumped. In one embodiment of the invention the pump is controlled to fill the tray with about 250 ml of fluid in a time of about 45 seconds. During filling the tray may be held fixed at the filling/emptying angle; however, it is preferable that the tray be rocked as filling proceeds.

In the processing step the motor alternately raises and lowers the end walls through a preselected optimum rocking angle (FIG. 2A, 155) at a preselected rocking frequency, for a preselected processing time. In one embodiment of the invention the maximum rocking angle 155 is about 2°, and the rocking frequency is about 30 rocks per minute. Optionally, during the processing step the control system may additionally control a heater or cooler, and a temperature monitor to control the temperature of the fluid.

In the emptying step the tray is held fixed with the port 145 below the horizontal and the tray making a filling/emptying angle 165 with the horizontal. The control system controls the control valve to select a waste container into which the fluid will be pumped and the control system then controls the pump to pump fluid from the tray into the selected container. There are at least three methods to ensure that the tray is completely emptied of fluid: first, the pump may be controlled to pump for a preselected length of time; second, the pump may be controlled to pump until a preselected volume of fluid has been pumped; and third, the pump may be controlled to pump until no more fluid is flowing. If the pump is controlled to pump a preselected volume of fluid the apparatus must further include a flow sensor to measure the volume of fluid pumped. Also, if the pump is controlled to pump until no fluid flows, the apparatus must further include a flow sensor to measure flow rate of the fluid. In one embodiment the tray is emptied of about 250 ml of fluid in about 45 seconds. During emptying the tray may be held fixed at the filling/emptying angle; however, it is preferable that the tray initially be held fixed at an angle less than the filling/emptying angle and subsequently be held fixed at the filling/emptying angle. In one embodiment the tray was emptied of about 250 ml of fluid in about 50 seconds by being held fixed at an angle of about 1.5° for about 30 seconds and then being held at a filling/draining angle of about 5° for about 20 seconds.

The following examples are included to show protocols that may be carried out using apparatus of the invention. As can be seen from the number of steps in the known protocols, the automatic fluid processing apparatus of the invention can be used to advantage, since manual filling and draining of the reagents is less efficient. In all protocols the steps are conducted at room temperature and the volume of solution used is about 250 mL.

EXAMPLE PROTOCOL 1

To silver stain unbacked SDS-PAGE gels 1.0 mm in thickness.

| Step # | Reagent | Time |
|---|---|---|
| 1 | Fixation solution | 30 min. |
| 2 | Sensitizing solution | 30 min. |
| 3–5 | Water washes+ | 3 × 5 min. |
| 6 | Silver reaction solution | 20 min. |
| 7–8 | Water washes | 2 × 1 min. |
| 9 | Developing solution | 4 min. |
| 10 | Stopping solution | 10 min. |
| 11–13 | Water washes+ | 3 × 5 min. |
| 14–15 | Preserving solution for unbacked gels | 2 × 30 min. |

+All water washes are carried out using deionized water.

Preparation of solutions is described in Pharmacia Biotech's Plus One® protein silver staining kit instructions.

EXAMPLE PROTOCOL 2

To Coomassie stain unbacked SDS-PAGE gels 1.0 mm in thickness.

| Step # | Reagent | Time |
|---|---|---|
| 1 | Fixation solution | 20 min. |
| 2 | Destain solution | 2 min. |
| 3 | 0.02% Coomassie stain | 60 min. |
| 4 | Destain solution | 10 min. |
| 5–10 | Destain solutions | 6 × 20 min. |
| 11–12 | Preserving solutions for unbacked gels | 2 × 30 min. |

Preparation of solutions is described in the instructions for Pharmacia Biotech's PhastGel® Blue tablets.

EXAMPLE PROTOCOL 3

To silver stain Pharmacia Biotech CleanGels® (backed) and 1 mm thick unbacked TBE-acrylamide gels.

| Step # | Reagent | Time |
|---|---|---|
| 1 | Fixation solution | 30 min. |
| 2–4 | Water washes+ | 3 × 2 min. |
| 5 | Silver Reaction solution | 20 min. |
| 6 | Water wash+ | 1 min. |
| 7 | Developing solution | 3 min. |
| 8 | Stopping solution | 10 min. |
| 9 | Preserving solution for backed gels or | 20 min. |
| 9–10 | Preserving solution for unbacked gels | 2 × 30 min. |

+Water washes use deionized water.

Preparation of solutions is described in Pharmacia Biotech's PlusOne® DNA silver stain kit instructions.

COMPARATIVE EXAMPLE 1: MIXING EFFICIENCY

To compare the mixing efficiency of an embodiment of the present invention and conventional apparatus, the following comparative test was carried out.

For each mixing apparatus, the tray was held steady in a horizontal plane and filled with about 250 mL of water. When the water had settled, a small drop of dye was placed in the center of the tray and the mixing was commenced. The mixing time, which was defined as the time at which the dye had completely dispersed throughout the water, was then recorded for each apparatus.

These tests were conducted using the Red Rocker (conventional rocker), the Red Rotor (conventional shaker) —both manufactured for Hoefer Pharmacia Biotech—and an embodiment of the present invention. The rocking frequency for both the present invention and the conventional rocker was about 30 rocks per minute; the rocking angle was about 2° for the present invention and about 8° for the conventional rocker. For the conventional shaker, the shaking frequency was about 50 rotations per minute and the shaking amplitude, i.e. the distance moved in the x and y directions, was about 1 inch.

| Mixing Apparatus | Mixing Time |
|---|---|
| Present Invention | ~28 sec. |
| Conventional Rocker | ~1 minute |
| Conventional Rocker | ≥1 minute (faint dye spot remains in center of tray) |

This example shows that a tray shaped as in FIG. 1 accomplishes the same level of mixing as conventional rockers and shakers in less than half the time.

In light of the foregoing, it can be seen that the invention overcomes problems encountered with conventional apparatus in two ways: first, it provides a means for containing a fluid and a workpiece that includes a tray shaped so as to more efficiently mix the fluid when the tray is rocked from side to side; and second, it provides for automatic filling and emptying of the tray.

While the invention has been described with respect to staining of electrophoresis gels, the efficiencies gained using the apparatus are expected to be applicable to other processes in which articles are exposed using fluids. Such applications include detection of biological molecules blotted or filtered onto a sheet of filter material, and photographic sheet or film processing.

What is claimed is:

1. An apparatus for circulating a fluid across a workpiece, the apparatus comprising:
   (a) means for containing a fluid and a workpiece, the means including a tray having first and second side walls, first and second end walls, a first curved wall portion connecting the first side wall and the first end wall, and a second curved wall portion connecting the second side wall and the second end wall, the means further including an imaginary plane extending from the first side wall and an imaginary plane extending from the first end wall, the planes intersecting with an inner angle of greater than 90°; and
   (b) means for alternately raising and lowering each end wall thereby causing the fluid to alternately flow towards and away from each end wall.

2. The apparatus according to claim 1, wherein the first and second end walls are parallel and the first and second side walls are parallel.

3. The apparatus according to claim 1, wherein the end walls have approximately equal lengths and the curved wall portions have approximately equal lengths, the length of the end walls being approximately equal to the length of the curved wall portions.

4. The apparatus according to claim 1, wherein the end walls have approximately equal lengths and the curved wall portions have approximately 7 equal lengths and the ratio of the length of the end walls to the length of the curved wall portions is from about 2:3 to about 3:2.

5. The apparatus according to claim 1, wherein the tray further includes a base having one or more ports.

6. The apparatus according to claim 1, wherein the means for containing the fluid and workpiece further includes a platform for supporting the tray.

7. The apparatus according to claim 6, wherein the means for alternately raising and lowering each end wall of the tray is connected to the platform and rocks the platform thereby alternately raising and lowering each end wall of the tray.

8. The apparatus according to claim 1, wherein the tray base and a lower portion of each tray wall are joined by a curved connection.

9. The apparatus according to claim 1, wherein the means for alternately raising and lowering each end wall of the tray includes:
   (a) a member for supporting an end of the tray;
   (b) a pivot for supporting the tray; and
   (c) a motor connected to the member for alternately rotating the member in a clockwise and an anticlockwise direction thereby alternately raising and lowering the end of the tray.

10. An apparatus for circulating a fluid across a workpiece, the fluid being supplied from, and discharged into a plurality of containers, the apparatus comprising:
   (a) means for containing a fluid and a workpiece, the means including a tray having first and second end walls, the tray having a base having one or more ports for adding and removing the fluid;
   (b) means for alternately raising and lowering each end wall thereby causing the fluid to alternately flow towards and away from each end wall; and
   (c) means for filling the tray with fluid from a selected one of said containers and emptying the tray of fluid into a selected one of said containers wherein each of said containers can be selected for emptying the tray.

11. The apparatus according to claim 10, wherein the means for alternately raising and lowering each end wall of the tray includes:
   (a) a member for supporting an end of the tray;
   (b) a pivot for supporting the tray; and
   (c) a motor connected to the member for alternately rotating the member in a clockwise and an anticlockwise direction thereby alternately raising and lowering the end of the tray and rocking the tray about the pivot.

12. The apparatus according to claim 10, wherein the tray further includes first and second side walls, a first curved wall portion connecting the first side wall and the first end wall, a second curved wall portion connecting the second side wall and the second end wall.

13. The apparatus according to claim 12, wherein the end walls both have approximately equal lengths and the curved wall portions both have approximately equal lengths, the length of the end walls being approximately equal to the length of the curved wall portions.

14. The apparatus according to claim 12, wherein the first and second end walls are parallel and the first and second side walls are parallel.

15. The apparatus according to claim 14, wherein an imaginary plane extending from the first side wall and an imaginary plane extending from the first end wall intersect with an inner angle of greater than 90°.

16. The apparatus according to claim 10, the apparatus further comprising:
   (d) a reagent container in fluid communication with the tray; and
   (e) a waste container in fluid communication with the tray;
   wherein the means for filling and emptying the tray fills the tray with fluid from the reagent container and empties the tray of fluid into the waste container.

17. The apparatus according to claim 16, wherein the means for filling and emptying the tray comprises:
   (a) a control valve for selectively connecting one of the containers to the tray port;
   (b) a fluid communication line connecting the tray port and the control valve; and
   (c) a pump connected in-line between the tray port and the control valve.

18. The apparatus according to claim 17, wherein the control valve includes a port connected to the fluid communication line and reagent and waste ports connected to reagent and waste container lines leading to reagent and waste containers respectively.

19. The apparatus according to claim 17, further comprising: a control system coupled to the means for alternately raising and lowering the end walls, the pump, and the control valve, for controlling one or more cycles comprising a filling step, a processing step, and an emptying step such that during a filling step the pump and control valve are controlled to fill the tray with fluid from the reagent container, during a processing step the means for alternately raising and lowering the end walls is controlled to alternately raise and lower the end walls and during an emptying step the pump and control valve are controlled to empty the tray of fluid into the waste container.

20. The apparatus according to claim 19 further comprising:
   (a) a heater mounted on the tray for heating the fluid or a cooler mounted on the tray for cooling the fluid; and
   (b) a temperature monitor mounted on the tray for monitoring the temperature of the fluid; and
   wherein the control system is coupled to the heater or cooler and the temperature monitor for controlling the temperature of the fluid.

21. The apparatus according to claim 19, further comprising:
(a) a flow sensor mounted in or on the fluid communication line for sensing the flow of fluid in the fluid communication line during a filling/emptying step; and wherein the control system is coupled to the flow sensor for controlling the flow of the fluid.

22. A tray for containing and mixing fluids, the tray having a base, first and second side walls, first and second end walls, a first curved wall portion connecting the first side wall and the first end wall, and a second curved wall portion connecting the second side wall and the second end wall; the base, first and second side walls, first and second end walls, and first and second curved wall portions defining a fluid mixing area throughout which a fluid may flow; and the tray further having an imaginary plane extending from the first side wall and an imaginary plane extending from the first end wall, the planes intersecting with an inner angle of greater than 90°.

23. The tray according to claim 22, wherein the first and second end walls are parallel and the first and second side walls are parallel.

24. The tray according to claim 22, wherein the end walls have approximately equal lengths and the curved wall portions have approximately equal lengths, the length of the end walls being approximately equal to the length of the curved wall portions.

25. The tray according to claim 22, wherein the end walls have approximately equal lengths and the curved wall portions have approximately equal lengths and the ratio of the length of the end walls to the length of the curved wall portions is from about 2:3 to about 3:2.

26. The tray according to claim 22, wherein the base has one or more ports for adding and removing the fluid.

27. The tray according to claim 22, wherein the tray base and a lower portion of each tray wall are joined by a curved connection.

28. A tray for containing and mixing fluids, the tray having a base, including at least one opening for the passage of fluids therethrough, first and second side walls, first and second end walls, a first curved wall portion connecting the first side wall and the first end wall, and a second curved wall portion connecting the second side wall and the second end wall, wherein the first and second end walls are parallel and the first and second side walls are parallel and wherein an imaginary plane extending from the first side wall and an imaginary plane extending from the first end wall intersect with an inner angle of greater than 90°.

29. An apparatus for circulating a fluid across a workpiece, the apparatus comprising:
(a) means for containing a fluid and a workpiece, the means including a tray having first and second side walls, first and second end walls, a first curved wall portion connecting the first side wall and the first end wall, and a second curved wall portion connecting the second side wall and the second end wall; and
(b) means for alternately raising and lowering each end wall thereby causing the fluid to alternately flow towards and away from each end wall;
wherein
the first and second end walls are parallel; the first and second side walls are parallel and an imaginary plane extending from the first side wall and an imaginary plane extending from the first end wall intersect with an inner angle of greater than 90°.

30. An apparatus for circulating a fluid across a workpiece, the apparatus comprising:
(a) means for containing a fluid and a workpiece, the means including a tray having first and second side walls, first and second end walls, a first curved wall portion connecting the first side wall and the first end wall, and a second curved wall portion connecting the second side wall and the second end wall, the end walls having approximately equal lengths and the curved wall portions having approximately equal lengths and the ratio of the length of the end walls to the length of the curved wall portions being from about 2:3 to about 3:2; and
(b) means for alternately raising and lowering each end wall thereby causing the fluid to alternately flow towards and away from each end wall.

31. The apparatus according to claim 30, wherein the length of the end walls is approximately equal to the length of the curved wall portions.

* * * * *

UNITED STATES PATENT AND TRADEMARK OFFICE
CERTIFICATE OF CORRECTION

PATENT NO. : 5,674,006
DATED : October 7, 1997
INVENTOR(S) : MOHAMMED REZAUL ISLAM ET AL.

It is certified that error appears in the above-identified patent and that said Letters Patent is hereby corrected as shown below:

Column 4, line 13, change "FIG. 4" to "FIG. 3"

Column 10, line 47, change "Rocker" to "Shaker"

Claim 4, Column 11, line 26, delete "7"

Signed and Sealed this

Twenty-fourth Day of February, 1998

Attest:

BRUCE LEHMAN

*Attesting Officer*         *Commissioner of Patents and Trademarks*